United States Patent [19]

O'Hara et al.

[11] Patent Number: 5,179,936

[45] Date of Patent: * Jan. 19, 1993

[54] DISPOSABLE SPECULUM WITH MEMBRANE BONDING RING

[75] Inventors: Gary J. O'Hara, Escondido, Calif.; David B. Phillips, Westford, Vt.; Kishan G. Hingorani, Irvine, Calif.

[73] Assignee: Intelligent Medical Systems, Inc., Carlsbad, Calif.

[*] Notice: The portion of the term of this patent subsequent to May 5, 2004 has been disclaimed.

[21] Appl. No.: 45,603

[22] Filed: Apr. 30, 1987

Related U.S. Application Data

[63] Continuation-in-part of Ser. No. 731,795, May 8, 1985, Pat. No. 4,662,360, which is a continuation-in-part of Ser. No. 663,769, Oct. 23, 1984, Pat. No. 4,602,642.

[51] Int. Cl.⁵ .......................... A61B 1/22; G01K 1/08
[52] U.S. Cl. ........................................ 128/9; 128/664; 374/158
[58] Field of Search .................. 128/9, 763, 664, 666, 128/4, 5; D10/57; 250/338; 374/126, 129, 158, 209, 120, 121

[56] References Cited

U.S. PATENT DOCUMENTS

| | | | |
|---|---|---|---|
| D. 218,851 | 9/1970 | Sato | D52/7 |
| 3,282,106 | 11/1966 | Barnes | 73/355 |
| 3,581,570 | 6/1971 | Wortz | 73/355 R |
| 3,681,991 | 9/1972 | Eberly, Jr. | 73/362 AR |
| 3,738,173 | 3/1973 | Sato | 73/343 R |
| 3,878,836 | 4/1975 | Twentier | 128/9 |
| 3,942,891 | 4/1976 | Spielberger et al. | 356/43 |
| 4,159,766 | 7/1979 | Kluge | 206/306 |
| 4,271,358 | 6/1981 | Schwarz | 250/338 |
| 4,380,998 | 4/1983 | Kieffer, III et al. | 128/9 |
| 4,602,642 | 7/1986 | O'Hara et al. | 128/664 |
| 4,634,294 | 1/1987 | Christol et al. | 374/170 |
| 4,662,360 | 5/1987 | O'Hara et al. | 128/9 |
| 4,784,149 | 11/1988 | Berman et al. | 128/664 |

FOREIGN PATENT DOCUMENTS

| | | |
|---|---|---|
| 2167973 | 8/1973 | France . |
| 2343234 | 9/1977 | France . |
| 1425765 | 2/1976 | United Kingdom . |
| 1518521 | 7/1978 | United Kingdom . |

OTHER PUBLICATIONS

Knoll; Radiation Detection and Measurement; 1979 pp. 68-71.

Proposed Standards E20-D-148, Clinical Thermometers Probe Covers and Sheaths, ASTM Nov. 28, 1984.

J. W. Moore and R. S. Newbower, "Noncontact Tympanic Thermometer", Medical and Biological Engineering & Computing, Sep. 1978, pp. 580-584.

Primary Examiner—Mark Graham
Attorney, Agent, or Firm—Baker, Maxham, Jester & Meador

[57] ABSTRACT

A sanitary protective cover or sheath for the ear canal probe of a tympanic thermometer. The speculum has a generally tubular body portion and an infrared transparent membrane attached to and sealing the forward end of the body portion. While the tubular body portion is being injection molded of plastic material such as polypropylene or polyethylene, a film of a similar plastic materil is mated to the forward end of the membrane and is thus severed from the film and one side thereof thermally bonded to the tubular body portion. At the same time a bonding ring of roughly the same diameter as the forward end of the tubular body portion is injection molded. The ring is thermally bonded to the opposite side of the film in alignment with the forward end of the tubular body portion.

10 Claims, 1 Drawing Sheet

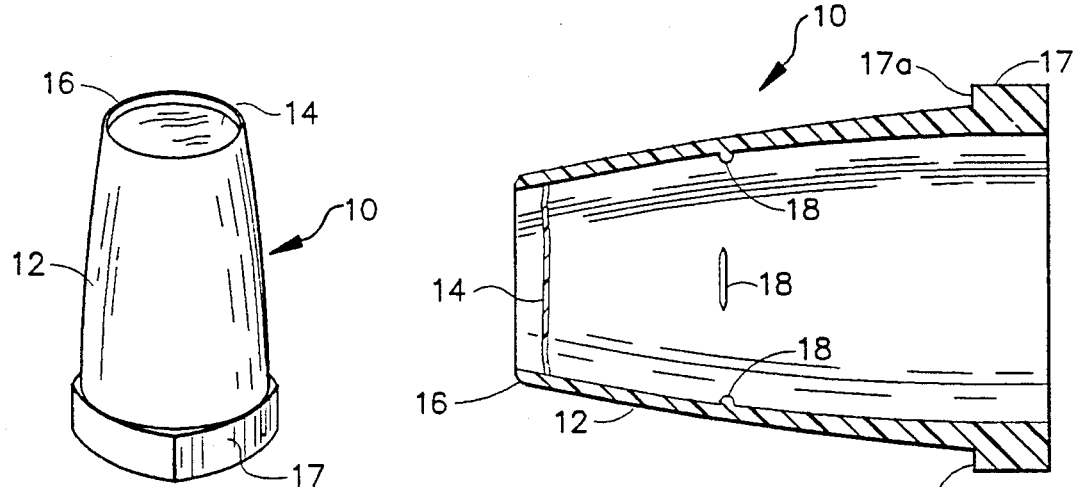
FIG. 1
FIG. 2
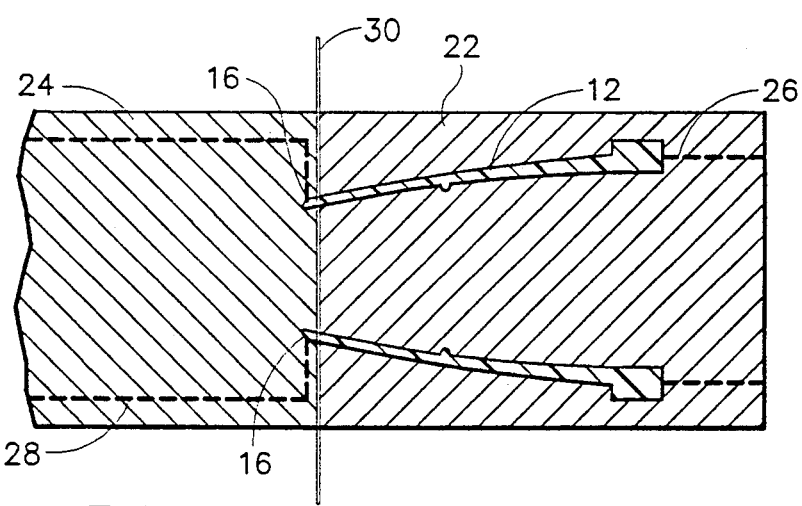
FIG. 3
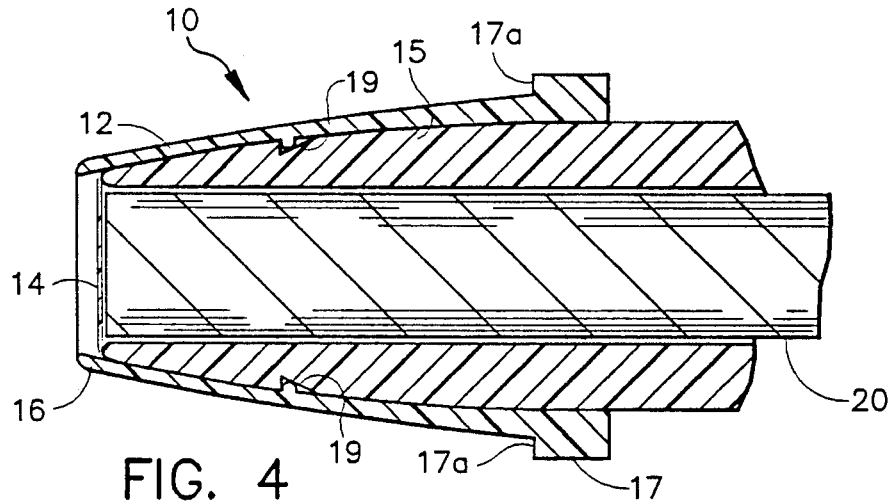
FIG. 4

DISPOSABLE SPECULUM WITH MEMBRANE BONDING RING

CROSS-REFERENCE TO RELATED APPLICATIONS

This is a continuation-in-part of prior pending U.S. patent application Ser. No. 731,795 filed May 8, 1985 and entitled "Disposable Speculum" which is now U.S. Pat. No. 4,662,360 granted May 5, 1987 which was in turn a continuation-in-part of prior U.S. patent application Ser. No. 663,769 filed Oct. 23, 1984 and entitled "Method and apparatus for Measuring Internal Body Temperature Utilizing Infrared Emissions" which is now U.S. Pat. No. 4,602,642 granted Jul. 29, 1986.

BACKGROUND OF THE INVENTION

The present invention relates to medical instruments, and more particularly, to a disposable cover or sheath for the probe of a clinical thermometer.

The diagnosis and treatment of many body ailments depends upon an accurate reading of the internal or core temperature of a patient's body, and in some instances, upon a comparison to a previous body temperature reading. For many years, the most common way of taking a patient's temperature involved the utilization of a Mercury thermometer. This approach has a number of drawbacks. First of all, such thermometers are normally made of glass. They must be inserted and maintained in the patient's mouth or rectum for several minutes. This is often discomforting to the patient. Furthermore, such thermometers can break, resulting in serious lacerations or Mercury poisoning. In addition, Mercury thermometers are difficult to read, must be sterilized, and must be "shaken down" vigorously to place the Mercury at the bottom end prior to use.

Because of the above drawbacks of conventional Mercury thermometers, electronic thermometers were developed and are now in widespread use. Typically, the commercialized versions of such electronic thermometers have been designed for taking a patient's temperature orally or rectally. They have a probe connected by wires to a remote unit containing an electronic circuit. The probe is inserted into a protective, disposable plastic cover or sheath before being inserted into the patient's mouth or rectum. After the patient's temperature is taken, the sheath is discarded, and the probe is inserted into another sanitary sheath for taking the next patient's temperature. In this manner, the electronic thermometer is rapidly reusable without communicating infectious organisms between patients.

The foregoing type of electronic thermometer typically uses predictive techniques, by which the patient's temperature reading is taken in a significantly shorter time period, for example thirty seconds, compared to the several minutes required for the conventional Mercury thermometers. Such electronic thermometers normally have meters or other displays which enable the operator to determine the temperature much more readily than reading the position of the terminal end of a column of Mercury inside a glass tube. The probe is typically an elongated rod of small diameter. The sheath comprises a hollow tube having an open end and a closed, somewhat pointed end. It has a round cross-section of relatively small diameter and is made of a plastic material which is not toxic.

The tympanic membrane is generally considered by the medical community to be superior to oral, rectal or auxiliary sites for taking a patient's temperature. This is because the tympanic membrane is more representative of the body's internal or core temperature and more responsive to changes in core temperature. Heretofore, efforts to provide a method and apparatus for measuring the body temperature via the external ear canal have not been successful. One approach has been to use a thermister, thermocouple or some other type of device requiring physical contact with the tympanic membrane. This approach is undesirable because of the discomfort to the patient and the danger of physical injury to the tympanic membrane. Another approach has directed air against the tympanic membrane and attempted to measure the increase in temperature in returning air in order to derive the patient's temperature. Clearly this approach has significant drawbacks in regard to accuracy. A third and better approach to tympanic temperature measurement involves sensing infrared emissions in the external ear canal. In order to accomplish this efficiently, a probe must be partially inserted into the external ear canal. A cover or sheath must be provided for enclosing the frontal portion of the probe to present a clean, sanitary surface to the patient and also to keep the probe free of ear wax and hair. The probe cover or sheath must be made of material which is substantially transparent to infrared radiation.

As used herein, the term "speculum" shall include any type of cover or sheath adapted to fit over a probe for the purpose just described. Preferably, such a speculum is inexpensive so that it can be disposed after a temperature reading has been taken and a new speculum installed over the probe for the next patient. This eliminates any need to sterilize such speculums.

Barnes U.S. Pat. No. 3,282,106 suggests the concept of an infrared thermometer that may be placed in the ear cavity to measure body temperature. An infrared detector receives radiation through an internally polished truncated cone which acts as a shield and which is partially inserted into the ear canal. This cone is apparently a permanent part of the apparatus and is not removable or disposable. The specification of the Barnes patent indicates that this cone was not intended to actually touch any portion of the outer ear. However, Barnes indicates that the cone may lightly touch portions of the outer ear because of lack of skill of the operator. Nevertheless, no protective speculum for the cone is disclosed in Barnes. The aforementioned Barnes patent also discloses an alternate embodiment including a conventionally shaped ear plug which contacts the external ear canal but is not provided with a speculum.

Wortz U.S. Pat. No. 3,581,570 discloses a tympanic temperature sensing device which has positioning means to establish a fixed relationship between the eardrum and a radiometer. A polyethylene shield fits over the probe portion to protect the radiometer. It does not appear that the shield is readily replaceable. Furthermore, the shield appears to be a cup-shaped member of uniform thickness. The very small width and length of the cup-shaped shield would make it very difficult to handle, install and replace.

Twentier U S. Pat. No. 3,878,836 discloses a disposable speculum for an infrared sensing tympanic thermometer. This speculum has the general shape of a funnel and has open forward and rearward ends. The patent indicates that preferably the speculum is formed of polyethylene. The principal drawback of this speculum is that its open forward end which is partially inserted into the ear canal may become clogged with wax or other debris and impair proper functioning. Also, the open forward end will permit germs and other foreign matter to be transferred to the thermometer instrument itself, thus presenting a risk of contamination and spreading of bacteria and viruses between patients.

A proposed ASTM standard for probe covers for body temperature thermometers refers to a minimum rupture pressure of 1.2 PSI. No specific construction for a probe cover is described in the ASTM standard.

SUMMARY OF THE INVENTION

Accordingly, it is the primary object of the present invention to provide an improved, disposable speculum.

It is another object of the present invention to provide a disposable speculum for the ear canal probe of a tympanic thermometer.

Another object of the present invention is to provide a disposable speculum configured for easy mounting and removal from the instrument probe.

Another object of the present invention is to provide a method of fabricating a disposable speculum uniquely suited for an infrared body temperature measuring instrument.

Another object of the present invention is to provide a disposable speculum which acts as a sanitary barrier between a patient's ear canal and the sensing portion of an infrared sensitive tympanic thermometer which is partially inserted into the external ear canal after having the speculum mounted over the same.

The disposable speculum of the present invention comprises a sanitary protective cover or sheath for the ear canal probe of a tympanic thermometer. The speculum has a generally tubular body portion and an infrared transparent membrane attached to and sealing the forward end of the body portion. While the tubular body portion is being injection molded of plastic material such a polypropylene or polyethylene, a film of a similar plastic material is mated to the forward end of the membrane and is thus severed from the film and one side thereof thermally bonded to the tubular body portion. At the same time a bonding ring of roughly the same diameter as the forward end of the tubular body portion is injection molded. The ring is thermally bonded to the opposite side of the film in alignment with the forward end of the tubular body portion.

BRIEF DESCRIPTION OF THE DRAWINGS

FIG. 1 is a perspective view of a preferred embodiment of the disposable speculum of the present invention.

FIG. 2 is an enlarged longitudinal sectional view of the speculum of FIG. 1.

FIG. 3 is an enlarged longitudinal sectional view illustrating the molding of the speculum of FIG. 1.

FIG. 4 is an enlarged longitudinal sectional view illustrating the speculum of FIG. 1 mounted over the probe of a tympanic thermometer.

DESCRIPTION OF THE PREFERRED EMBODIMENT

Referring to FIGS. 1 and 2, the preferred embodiment 10 of our disposable speculum includes a generally tubular body portion 12 and an infrared transparent membrane 14 attached to and sealing the forward end of the tubular body portion. A bonding ring 16 is connected to the periphery of the membrane 14 and extends forwardly therefrom.

The tubular body portion 12 and bonding ring 16 (FIG. 2) have a generally frusto-conical or truncated cone configuration. The diameter of the body portion gradually reduces from its rearward end to its forward end. The ring diameter conforms in shape and size to that of the body portion. The frusto-conical configuration of the combined body portion and ring permits the speculum to be partially inserted into the ear canals of both children and adults. The tapered configuration also enables the speculum to be snugly fit over and retained on the conformably shaped rigid plastic probe 15 (FIG. 4) of a tympanic thermometer instrument as explained hereafter in greater detail.

Our speculum 10 is preferably made of a non-toxic material since it will come into contact with a patient's skin. Also, the speculum is preferably made of a material which is somewhat pliant. This allows the speculum to deform slightly to facilitate insertion into the ear canal and also to squeeze fit over the instrument probe. Most importantly, the membrane 14 must be made of a material which is substantially transparent to infrared radiation, preferably in the seven to fifteen micron wavelength range, and more preferably substantially transparent to infrared radiation having a wavelength of approximately ten microns. Clinical data has confirmed that accurate internal body temperature readings can be made by sensing infrared radiation at the foregoing wavelength which is emitted in the external ear canal.

Polypropylene and polyethylene are both plastic materials which are substantially transparent to infrared radiation at the foregoing wavelength. Of course the amount of attenuation of the infrared radiation passing through this material depends upon the thickness thereof. Accordingly, the membrane 14 must be relatively thin to minimize the attenuation of infrared radiation passing therethrough so that the thermopile or other detector receiving infrared radiation through the membrane will sense the maximum amount of infrared radiation available. This enhances the accuracy of temperature measurement. Also, the membrane should have a uniform thickness, with no wrinkles or other structural characteristics that will distort the infrared radiation passing therethrough. Such distortion can introduce errors in the temperature measurement process.

Accordingly, in the preferred embodiment of our speculum, the membrane 14 (FIG. 2) which serves as the IR window is made of polypropylene or polyethylene film having a maximum thickness of 0.001 inches, and preferably a thickness in the range of 0.0005 to 0.001 inches. Preferably, the speculum will withstand approximately 1.2 PSI without rupturing or otherwise allowing fluid to leak through. As explained hereafter in greater detail, the membrane 14 is thermally bonded to the forward end of the tubular body portion 12 with the aid of the bonding ring 16 in order to ensure it will be able to withstand a minimum approximately 1.2 internal PSI. The bonding ring has a diameter substantially equal to that of the forward end of the tubular body portion. The ring 16 is bonded to one side of the membrane 14 and the other side of the ring is bonded to the forward end of the tubular body portion 12.

The tubular body portion 12 and bonding ring 16 (FIG. 2) of the speculum need not be made of an infrared transparent material. However, our speculum is more easily fabricated and the bond between the membrane and the body portion is optimized, if the membrane 14, bonding ring 16 and body portion 12 are made of a similar plastic material. The body portion must be sufficiently strong such that the speculum can be mounted over the probe, and removed from the probe, without the operator having to touch the speculum. This ensures that the speculum will be sanitary when it is introduced into the patient's ear canal. Accordingly, the thickness of the walls of the body portion 12 must be chosen to provide sufficient structural integrity to permit the foregoing mounting and removal from the instrument probe. By way of example, where the body portion is made of polypropylene or polyethylene, a wall thickness of between approximately 0.01 to 0.02 inches is adequate. Thus the preferred embodiment has a membrane thickness between approximately one-tenth and one-fortieth a thickness of the annular wall forming the body portion.

A rear shoulder 17 (FIG. 1) projects outwardly from the rear end of the tubular body portion. The faces 17a (FIG. 2) of the shoulder can engage a support well (not illustrated) in which the speculum rests. This holds the speculum stationary when the probe 15 of the infrared thermometer is inserted into the speculum. A plurality of circumferentially spaced ears 18 (FIG. 2) project inwardly from the interior of the tubular body portion and mate with corresponding detents 19 (FIG. 4) in the thermometer probe 15 for retaining the speculum on the probe.

By way of example, the outside diameter of the tubular body portion 12 may taper from an outside diameter of 0.50 inches immediately forward of the shoulder 17 to an outside diameter of 0.36 inches at the membrane 14. The tubular body portion 12 in its entirety may have a longitudinal dimension of 0.825 inches.

To facilitate shipment and use, a plurality of the speculums may be connected in an array of rows and columns by a tree structure (not illustrated) of interconnected rails and side walls made of the same plastic as the speculum body. This type of structure is illustrated in U.S. Pat. No. 4,662,360 granted May 5, 1987. Small integrally formed plastic extensions (not illustrated) may connect the tubular body portion of each of the speculums to the rails and side walls of the tree structure. These extensions can be configured and dimensioned to be easily broken to individually release a selected one of the speculums upon a predetermined amount of force being applied to the one speculum in a direction away from the tree structure while the tree structure is held in a stationary position.

The side walls of the aforementioned tree structure may be supported in a housing of a tympanic thermometer as illustrated in U.S. Pat. No. 4,602,642. Each speculum may also be seated in a corresponding well in the housing having walls which engage and support the shoulder faces 17a when the probe 15 of the thermometer is inserted into the rear end of the speculum and pushed downwardly toward the well. The speculum thus is squeezed over the probe and the ears 18 mate with the detents 19 of the probe 15. As this is done, the extensions break. The probe can then be withdrawn and the speculum is retained tightly thereon.

Preferably the body portion 12 of the speculum 10 mates with the probe 15 so that the membrane 14 is stretched tightly over the probe tip, thereby removing any wrinkles in the membrane. This is illustrated in FIG. 4. A predetermined longitudinal relationship is thus established between the body portion 12 and the probe 15. When the ears 18 mate with the detents 19 of the probe, the membrane 14 is held in tight, stretched fashion thereby preventing any wrinkles that would interfere with measurement accuracy. The tympanic thermometer has a gold plated wave guide tube 20 (FIG. 4) which extends concentrically within, and is spaced from the plastic probe 15. The outer end of this tube is preferably spaced closely behind the stretched membrane 14. The outer end of the tube 20 may be covered with another semi-permanent infrared transparent film (not illustrated).

The most convenient way to fabricate the preferred embodiment of our probe would be to injection mold the entire speculum in one integral piece. However, with current plastic molding technology and apparatus, we have found it difficult to integrally mold the entire speculum with the walls and the membrane having thicknesses in the ranges described above.

In order to overcome the foregoing problem, we have discovered that the preferred method of fabrication is to injection mold the tubular body portion and bonding ring 16 and to affix a separate membrane therebetween. A film of a similar plastic material as the tubular body portion and ring may be mated to the forward end of the tubular body portion and the aft end of the ring while the tubular body portion and ring are being injection molded. A portion of the film defining the membrane is thus severed from the film and thermally bonded to the tubular body portion and ring. The strength of the thermal bond is greatly enhanced if the body portion, film and ring are made of the same material. This is because they will then have the same melting point.

The diagrammatic view of FIG. 3 illustrates a preferred method of fabricating our speculum. A first mold portion 22 and a second mold portion 24 are mounted for mating engagement. They have cavities defining the shapes of the body portion 12 and bonding ring 16. Molten plastic is conveyed into these mold cavities through passages 26 and 28 in the mold portions. These passages are illustrated in phantom lines.

Molten plastic is injected into the mold cavities after the mold portions 22 and 24 are squeezed together with a web 30 of plastic film there between. The film is supported at each end on rollers (not illustrated) coupled to a mechanical drive (not illustrated).

The molten plastic which reaches the film 30 severs a circular portion thereof which becomes the membrane 14. The peripheral edges of this membrane thermally bond to the frontal end of the molten tubular body portion and the rearward end of the bonding ring.

The mold portion 22 is designed with separable parts (not illustrated) so that the body portion 12 may be removed once the mold portions have cooled and the plastic has hardened. The ring 16 and ears 18 are small and elastic. They can deform sufficiently to allow the now integrally formed body portions, membrane and ring to be withdrawn from the mold portions. Details of the molding apparatus have not been described as they will be apparent to those skilled in the plastic molding art.

Having described a preferred embodiment of our speculum and its method of fabrication, it should be apparent to those skilled in the art that our invention may be modified in both arrangement and detail. For example, the bonding ring 16 may be eliminated if the tubular body portion and membrane are otherwise configured to meet the desired internal PSI rupture standard. The body portion 12 and ring 16 need not have a circular configuration. Accordingly, the term "bonding member" as used in the claims shall refer to any auxiliary structure molded on the other side of the membrane in alignment with the forward end of the tubular body portion to aid in securing the membrane to the forward end of the tubular body portion. The term "bonding" as used herein encompasses not only melting and joining, but other joining techniques such as sonic welding and adhesive bonding. Therefore, the protection afforded our invention should only be limited in accordance with the scope of the following claims.

We claim:

1. A speculum comprising:
   a generally tubular body portion having forward and rearward ends;
   a membrane extending across the forward end of the tubular body portion, the membrane having a maximum thickness of approximately 0.001 inches and being substantially transparent to infrared radiation; and
   a bonding member ring joined to the membrane on a first side thereof opposite a second side which is bonded to the forward end of the tubular body portion.

2. A speculum comprising:
   a generally tubular body portion;
   a thin membrane attached to and extending across a forward end of the tubular body portion;
   the tubular body portion and the membrane being made of a material selected from the group consisting of polypropylene and polyethylene; and
   the membrane being wrinkled and having a thickness selected to minimize attenuation of infrared radiation passing therethrough when stretched tight.

3. A speculum comprising:
   a generally tubular body portion;
   a bonding member;
   a thin membrane having a first side extending across and connected to a forward end of the tubular body portion;
   the membrane being substantially transparent to infrared radiation;
   the bonding member being connected to a second side of the membrane in alignment with the forward end of the tubular body portion;
   the membrane, tubular body portion and bonding member being made of a plastic material; and
   the tubular body portion being injection molded, the membrane being formed of a separate film bonded to the forward end of the tubular body portion and the bonding member being injection molded and bonded to the membrane.

4. A speculum for a tympanic thermometer that rapidly senses infrared emissions in an external ear canal of a patient via a sensing probe, comprising:
   a generally tubular body portion configured and dimensioned to be inserted into an external ear canal of a patient after being removably mounted over a probe;
   an infrared transparent thin film membrane bonded to and extending across a forward end of the body portion;
   the body portion and the membrane being made of a same plastic material; and
   means for establishing a predetermined longitudinal relationship between the body portion and the probe such that the film membrane is stretched over a forward end of the probe to substantially remove any wrinkles otherwise present therein.

5. A speculum according to claim 4 wherein the means for establishing a predetermined longitudinal relationship includes a plurality of ears that project from an inner wall of the body portion and mate with a plurality of corresponding detents formed in an outer wall of the probe.

6. A speculum according to claim 4 and further comprising a bonding member joined to the membrane on a first side thereof opposite a second side which is bonded to the forward end of the body portion.

7. A speculum according to claim 6 wherein the bonding member is made of the same plastic material as the body portion and the membrane.

8. A speculum according to claim 6 wherein the bonding member is configured in the shape of a ring.

9. A speculum comprising:
   a generally tubular body portion;
   a bonding member;
   a thin membrane having a first side extending across and connected to a forward end of the tubular body portion;
   the membrane being substantially transparent to infrared radiation;
   the bonding member being connected to a second side of the membrane in alignment with the forward end of the tubular body portion; and
   the membrane, tubular body portion and bonding member being made of a plastic material.

10. A speculum for a tympanic thermometer that rapidly determines an internal body temperature of a patient by sensing infrared emissions in an external ear canal of the patient, comprising:
    a pliant, tubular, frusto-conical body portion configured and dimensioned to be inserted into an external ear canal of a patient after being removably mounted over a probe of the thermometer, the body portion being formed of an annular wall having a thickness of approximately 0.01 to 0.02 inches, the body portion including a plurality of circumferentially spaced ears that project radially inwardly from an inner wall of the body portion and adapted to mate with a plurality of corresponding detents formed in an outer wall of the probe to retain the body portion over the probe, and the body portion further having a forwardly facing shoulder that projects radially outwardly from a rearward end of the body portion;
    a thin film membrane thermally bonded to and extending across a forward end of the body portion and having a substantially uniform thickness of between approximately 0.005 and 0.001 inches, the film membrane being substantially transparent to infrared radiation in the seven to fifteen micron wavelength range;
    a longitudinal dimension of the body portion being at least twice a transverse dimension of the membrane;
    a bonding ring thermally bonded to the membrane on a first side thereof opposite a second side which is thermally bonded to the forward end of the body portion, the bonding ring aiding in securing the membrane to the forward end of the probe;
    the body portion, the membrane and the ring being made of a material selected from the group consisting of polypropylene and polyethylene;

the membrane being capable of withstanding approximately 1.2 PSI without rupturing, leaking or unbonding from the forward end of the body portion;

the ears being located on the inner wall of the body portion at positions such that when the ears mate with the detents formed in the outer wall of the probe, the film membrane is stretched over the forward end of the probe to substantially remove any wrinkles otherwise present in the membrane whereby distortion in a measurement process of the tympanic thermometer will be minimized; and the longitudinal dimension of the body portion being sufficient to prevent direct contact between the probe and the ear canal to thereby inhibit contamination of the probe.

* * * * *